(12) United States Patent
Gamage

(10) Patent No.: US 8,714,021 B2
(45) Date of Patent: May 6, 2014

(54) CATHETER DIE AND METHOD OF FABRICATING THE SAME

(75) Inventor: Sisira Kankanam Gamage, Palo Alto, CA (US)

(73) Assignee: Amphenol Thermometrics, Inc., Saint Marys, PA (US)

( * ) Notice: Subject to any disclaimer, the term of this patent is extended or adjusted under 35 U.S.C. 154(b) by 235 days.

(21) Appl. No.: 13/406,395

(22) Filed: Feb. 27, 2012

(65) Prior Publication Data

US 2013/0220972 A1 Aug. 29, 2013

(51) Int. Cl.
  *G01L 9/06* (2006.01)
  *B29C 47/92* (2006.01)
  *G01L 9/00* (2006.01)

(52) U.S. Cl.
  CPC ............ *G01L 9/0045* (2013.01); *G01L 9/0048* (2013.01); *G01L 9/0052* (2013.01)
  USPC .................. 73/721; 73/727; 216/39; 425/170

(58) Field of Classification Search
  CPC ... G01L 9/0048; G01L 9/0049; G01L 9/0054; B29C 47/0023; B29C 47/003; B29C 66/50
  See application file for complete search history.

(56) References Cited

U.S. PATENT DOCUMENTS

| | | | |
|---|---|---|---|
| 3,088,323 A * | 5/1963 | Welkowitz et al. ............. | 73/727 |
| 3,624,714 A | 11/1971 | Frassrand | |
| 4,685,469 A | 8/1987 | Keller | |
| 4,886,070 A | 12/1989 | Demarest | |
| 5,483,994 A | 1/1996 | Maurer | |
| 5,701,905 A | 12/1997 | Esch | |
| 6,019,728 A | 2/2000 | Iwata et al. | |
| 6,264,612 B1 | 7/2001 | McConnell et al. | |
| 6,959,608 B2 | 11/2005 | Bly et al. | |
| 6,973,835 B2 * | 12/2005 | Rangsten et al. ............... | 73/754 |
| 7,007,551 B2 | 3/2006 | Zdeblick et al. | |
| 7,013,734 B2 | 3/2006 | Zdeblick et al. | |
| 7,017,420 B2 | 3/2006 | Kalvesten et al. | |
| 7,028,550 B2 | 4/2006 | Zdeblick et al. | |
| 7,066,031 B2 | 6/2006 | Zdeblick et al. | |
| 7,073,387 B2 | 7/2006 | Zdeblick et al. | |
| 7,111,518 B1 | 9/2006 | Allen et al. | |
| 7,207,227 B2 * | 4/2007 | Rangsten et al. ............... | 73/754 |
| 7,265,429 B2 | 9/2007 | Wan | |
| 7,284,441 B2 | 10/2007 | Zdeblick | |
| 7,398,688 B2 | 7/2008 | Zdeblick et al. | |
| 7,539,003 B2 | 5/2009 | Ray et al. | |
| 7,642,115 B2 | 1/2010 | Eriksen et al. | |

(Continued)

OTHER PUBLICATIONS

Search Report and Written Opinion from PCT/US2013/027608 dated Jun. 19, 2013.

*Primary Examiner* — Andre Allen
(74) *Attorney, Agent, or Firm* — Blank Rome LLP

(57) ABSTRACT

A catheter die is provided and includes a device layer defining a cavity and including a piezoresistive pressure sensor operably disposed proximate to the cavity and an insulator having an opening and being disposed on an upper surface of the device layer such that a portion of the piezoresistive pressure sensor is exposed through the opening. The catheter die further includes an insulation layer bonded to a lower surface of the device layer and first and second bond pads, the first bond pad being electrically coupled to the portion of the piezoresistive pressure sensor via the opening and the second bond pad being disposed on the insulation layer.

20 Claims, 15 Drawing Sheets

(56) References Cited

U.S. PATENT DOCUMENTS

| | | |
|---|---|---|
| 7,762,138 B2 | 7/2010 | Zdeblick et al. |
| 7,911,315 B2 | 3/2011 | Bradley |
| 7,952,154 B2 | 5/2011 | Guo et al. |
| 8,013,405 B2 | 9/2011 | Eriksen et al. |
| 8,044,929 B2 | 10/2011 | Baldo et al. |
| 2003/0199085 A1 | 10/2003 | Berger et al. |
| 2005/0103114 A1 | 5/2005 | Bly et al. |
| 2005/0121734 A1 | 6/2005 | Degertekin et al. |
| 2005/0187487 A1 | 8/2005 | Azizkhan et al. |
| 2006/0117871 A1 | 6/2006 | Wilner |
| 2009/0036754 A1 | 2/2009 | Pons et al. |
| 2009/0203163 A1 | 8/2009 | Erkisen et al. |
| 2010/0230768 A1 | 9/2010 | Legat et al. |
| 2010/0308791 A1 | 12/2010 | Gowrishetty et al. |
| 2011/0256652 A1 | 10/2011 | Guo et al. |
| 2013/0259964 A1* | 10/2013 | Gamage ..................... 425/170 |

* cited by examiner

CATHETER DIE AND METHOD OF FABRICATING THE SAME

BACKGROUND OF THE INVENTION

The subject matter disclosed herein relates to a catheter die and a method of fabricating a catheter die for pressure sensing.

A pressure sensor measures pressure, typically of gases or liquids. Pressure is an expression of the force required to stop a fluid from expanding, and is usually stated in terms of force per unit area. A pressure sensor usually acts as a transducer in that it generates a signal as a function of the pressure imposed. Such a signal may be an electrical signal or current.

There are two basic categories of pressure sensors. These are force collector types, which generally use a force collector, such as a diaphragm, piston, bourdon tube, or bellows, to measure strain or deflection due to applied force or pressure over an area, and other types, which use other properties, such as density, to infer gas or liquid pressures. A piezoelectric pressure sensor is a force collector type of pressure sensor and uses the piezoelectric effect in certain materials, such as quartz, to measure the strain upon a sensing mechanism due to pressure.

BRIEF DESCRIPTION OF THE INVENTION

According to one aspect of the invention, a catheter die is provided and includes a device layer defining a cavity and including a piezoresistive pressure sensor operably disposed proximate to the cavity and an insulator having an opening and being disposed on an upper surface of the device layer such that a portion of the piezoresistive pressure sensor is exposed through the opening. The catheter die further includes an insulation layer bonded to a lower surface of the device layer and first and second bond pads, the first bond pad being electrically coupled to the portion of the piezoresistive pressure sensor via the opening and the second bond pad being disposed on the insulation layer.

According to another aspect of the invention, a catheter die is provided and includes a device layer defining a cavity and including a piezoresistive pressure sensor operably disposed proximate to the cavity and an insulator having an opening and being disposed on an upper surface of the device layer such that a portion of the piezoresistive pressure sensor is exposed through the opening, an insulation layer bonded to the lower surface of the device layer, a first bond pad electrically coupled to the portion of the piezoresistive pressure sensor via the opening, a second bond pad disposed on the insulation layer and electrically coupled to the first bond pad via wiring and an external connector electrically coupled to the second bond pad at a distance from the wiring.

According to yet another aspect of the invention, a method of fabricating a catheter die is provided and includes forming, in a device layer having upper and lower surfaces, a cavity recessed from at least the upper surface and a piezoresistive pressure sensor operably disposed proximate to the cavity, disposing an insulator having an opening on the device layer to expose a portion of the piezoresistive pressure sensor, bonding an insulation layer to the lower surface of the device layer and electrically coupling a first bond pad to the portion of the piezoresistive pressure sensor via the opening and disposing a second bond pad on the insulation layer.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
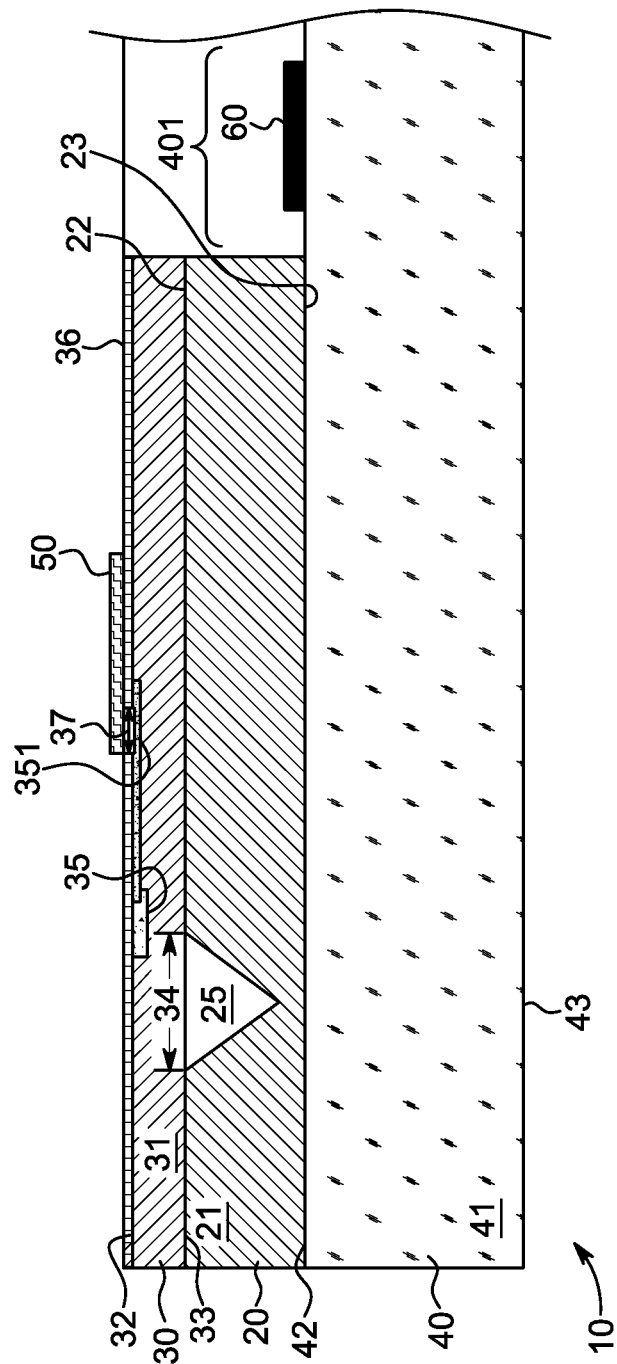
FIG. 1 is a side view of a catheter die in accordance with embodiments of the invention.

With reference to FIG. 1, a catheter die 10 is provided and includes a first device layer 20, a second device layer 30, an insulation layer 40, a first bond pad 50 and a second bond pad 60. The first device layer 20 has a main body 21 with an upper surface 22 and a lower surface 23 that opposes the upper surface 22. The first device layer 20 is also formed to define a cavity 25 therein, which is recessed from at least the upper surface 22.

The second device layer 30 has a main body 31 with an upper surface 32 and a lower surface 33 that opposes the upper surface 32. The lower surface 33 of the second device layer 30 is bonded to the upper surface 22 of the first device layer 20 to thereby seal the cavity 25 at least at the upper surface 22. The second device layer 30 further includes a diaphragm 34 defined above the cavity 25 and a piezoresistive pressure sensor 35, which is operably disposed proximate to the diaphragm 34 and the cavity 25, and an insulator 36. The insulator 36 is disposed on the upper surface 32 of the second device layer 30 and has an opening 37 defined therein, which exposes a portion 351 of the piezoresistive pressure sensor 35.

The insulation layer 40 has a main body 41 with an upper surface 42 and a lower surface 43 that opposes the upper surface 42. The upper surface 42 of the insulation layer 40 is bonded to the lower surface 23 of the first device layer 20 to provide for support, stability and strength of the catheter die 10. The first bond pad 50 is formed of electrically conductive material and is electrically coupled to the portion 351 of the piezoresistive pressure sensor 35 exposed via the opening 37. The second bond pad 60 is similarly formed of electrically conductive material and is disposed on the insulation layer 40. As will be described below with reference to FIG. 15, the first bond pad 50 and the second bond pad 60 may be electrically coupled to one another via a wire bond with the second bond pad 60 further electrically coupled to an external connection.

In accordance with embodiments, the insulation layer 40 is substantially larger in terms of surface area than the first device layer 20 or the second device layer 30. Thus, a portion 401 of the insulation layer 40 extends outwardly from borders of the first device layer 20 and the second device layer 30 such that the upper surface 42 may be at least partially exposed. The second bond pad 60 may be disposed, for example, on the portion of the upper surface 42 that is partially exposed. The second bond pad 60 may therefore be substantially longer than the first bond pad 50.

With this construction, the cavity 25 may be defined as a vacuum or with a known, predefined internal pressure. In either case, when the catheter die 10 is exposed to unknown atmospheric conditions, a pressure differential between an interior of the cavity 25 and an exterior of the catheter die 10 may be sufficient to cause the diaphragm 34 of the second device layer 30 to bend inwardly or outwardly depending on whether the pressure of the interior of the cavity 25 is low or higher than that of the exterior of the catheter die 10. This bending of the diaphragm 34 applies a strain to the piezoresistive pressure sensor 35 and induces a current therein. By coupling appropriate circuitry to the piezoresistive pressure sensor 35, a magnitude of this current can be determined and, thus, a pressure at the exterior of the cavity 25 can be calculated.

Figure 2:
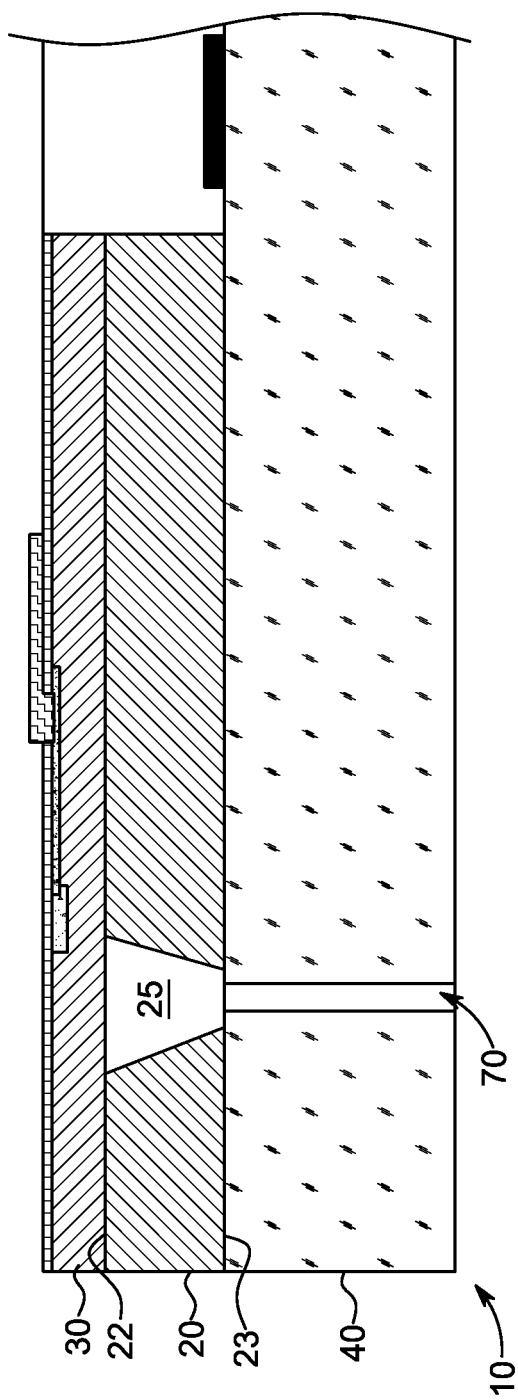
FIG. 2 is a side view of a catheter die in accordance with alternative embodiments of the invention.

In accordance with alternative embodiments and, with reference to FIG. 2, a vent channel 70 may be formed in the insulation layer 40. As shown in FIG. 2, the cavity 25 may be recessed from both the upper surface 22 and the lower surface 23 of the first device layer 20. The vent channel 70 may therefore be fluidly communicative with the cavity 25 via an interconnection proximate to the lower surface 23 such that a pressure within the cavity 25 can be actively controlled.

In accordance with further embodiments, it is to be understood that the first device layer 20 and the second device layer 30 may be formed or otherwise provided as a single device layer. Also, while a combined thickness of the first device layer 20 and the second device layer 30 may be approximately 390 µm or less, a thickness of the second device layer 30 may be approximately 1-4.5 µm or less. Similarly, a thickness of the insulation layer 40 may be approximately 390 µm or less although it is to be understood that at least this thickness can be substantially variable.

In accordance with still further embodiments, the first device layer 20 and the second device layer 30 may each be formed of a semi-conductive material, such as silicon, while the insulation layer 40 may be formed of glass or some other electrically non-conductive material.

With reference to FIGS. 3-15, a method of fabricating a catheter die as described above will be provided below. It is to be understood that, for purposes of clarity and brevity, the description will generally relate to the exemplary embodiments of the catheter die 10 shown in FIG. 1. The method of fabricating the catheter die 10 with the vent channel 70, as shown in FIG. 2, are substantially similar and need not be separately described.

Figure 3:
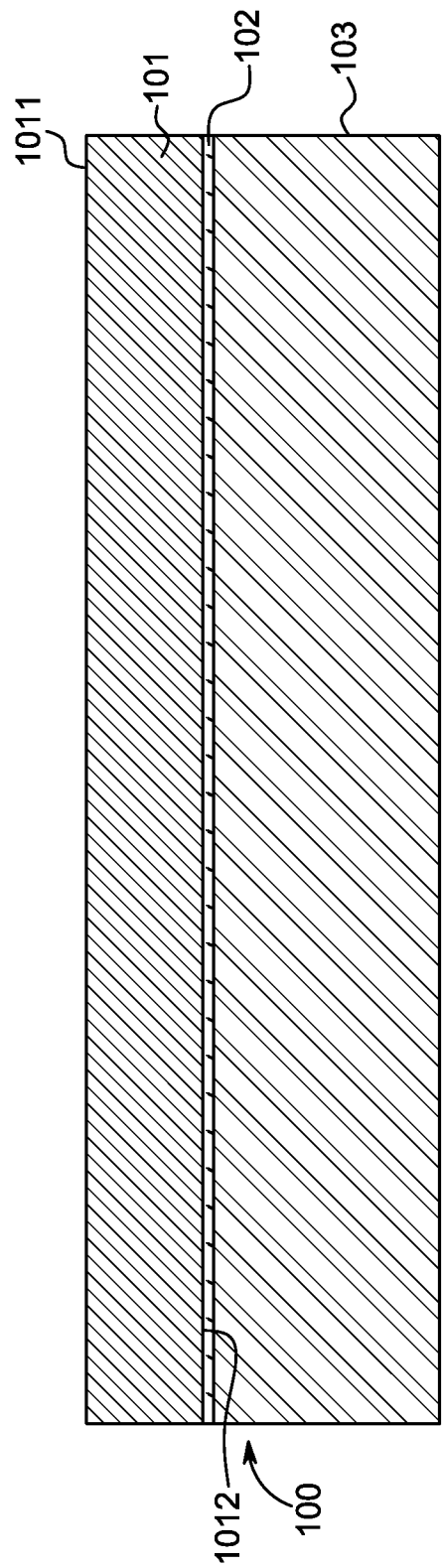
FIG. 3 is a side view of a wafer.
Figure 4:
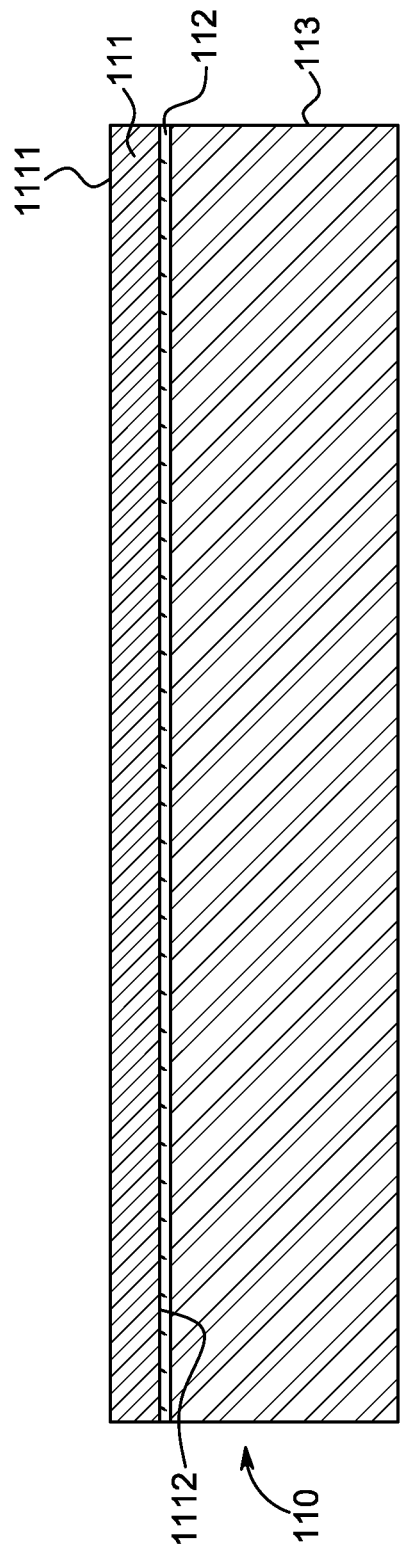
FIG. 4 is a side view of a wafer.

As shown in FIGS. 3 and 4, the method initially includes formation of a wafer 100 having a first device layer 101 (see FIG. 3) and a wafer 110 having a second device layer 111 (see FIG. 4). The wafer 100 may be formed as a silicon-on-insulator (SOI) wafer with the first device layer 101 having an upper surface 1011 and a lower surface 1012 and being formed of an n-type or p-type semi-conductor (i.e., silicon). The first device layer 101 is disposed on a first buried oxide layer 102, which is itself disposed on a first handle layer 103. The first handle layer 103 may be formed of an n-type or p-type semi-conductor. The wafer 110 may be formed as a silicon-on-insulator (SOI) wafer with the second device layer 111 having an upper surface 1111 and a lower surface 1112 and being formed of an n-type semi-conductor (i.e., silicon). The second device layer 111 is disposed on a second buried oxide layer 112, which is itself disposed on a second handle layer 113. The second handle layer 113 may be formed of an n-type or p-type semi-conductor.

Figure 5:
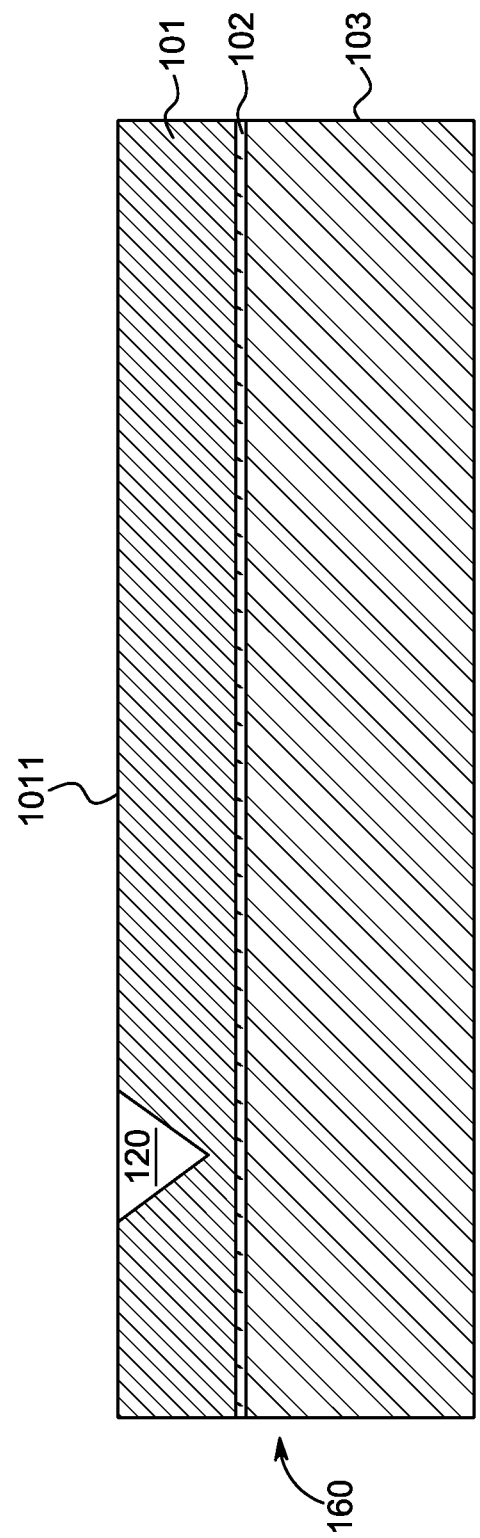
FIG. 5 is a side view of a cavity formed in the wafer of FIG. 3.

As shown in FIG. 5, a cavity 120 is formed in the first device layer 101. The cavity 120 is illustrated as being triangular and recessed from the upper surface 1011 of the first device layer 101 although, it is to be understood that this is merely exemplary and that the cavity 120 may have various shapes and sizes. In accordance with embodiments, the cavity 120 may be formed of a wet etch process, such as Potassium Hydroxide (KOH) etching or Tetramethylammonium Hydroxide (TMAH) etching, or a dry etch process, such as Deep Reactive Ion Etching (DRIE).

Figure 6:
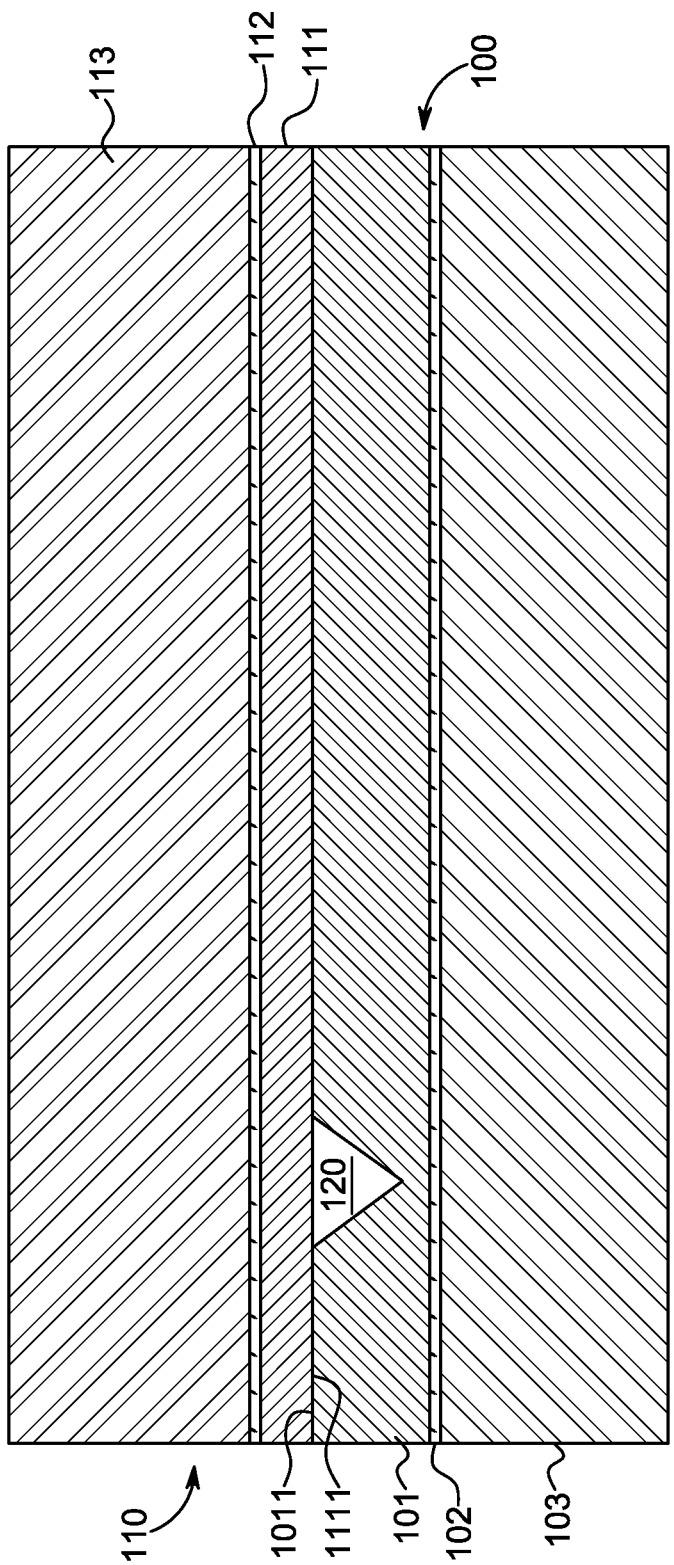
FIG. 6 is a side view of an assembly of the wafers of FIGS. 3 and 4.
Figure 7:
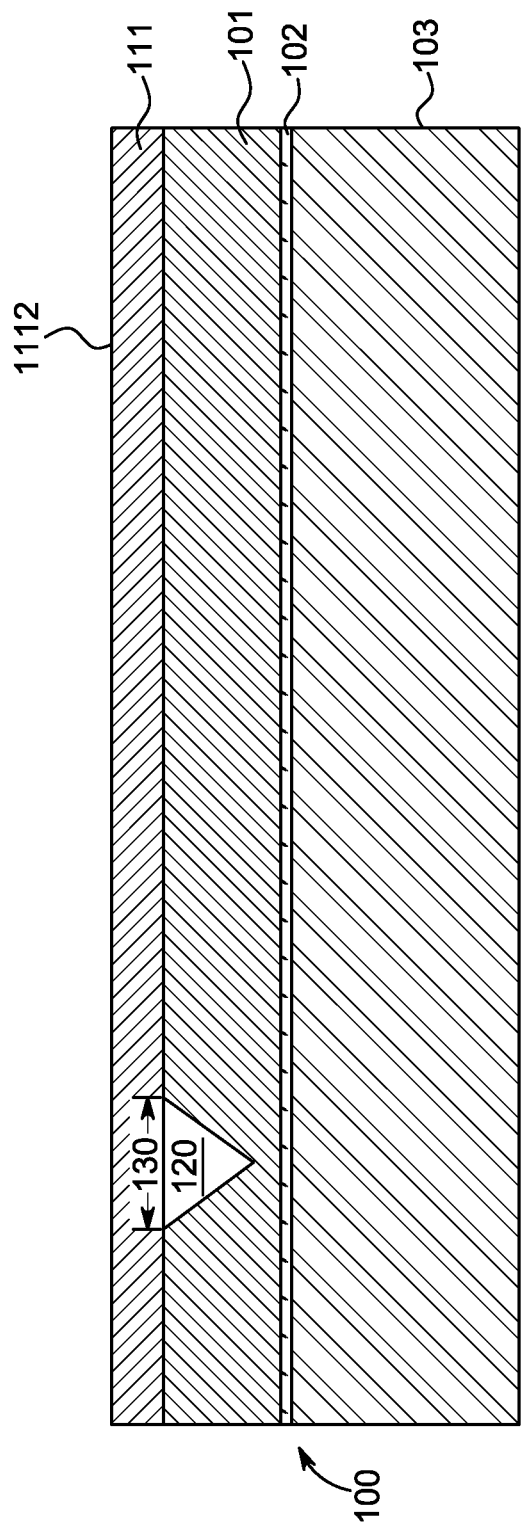
FIG. 7 is a side view of the assembly of FIG. 6 with layers removed.

With reference to FIGS. 6 and 7, the wafer 110 is inverted and the upper surface 1111 of the second device layer 111 is bonded with the upper surface 1011 of the first device layer 101 such that the second device layer 111 seals the cavity 120 at the upper surface 1011 of the first device layer 101 (see FIG. 6). This operation may be conducted as a silicon fusion bonding process at an elevated temperature of approximately 900-1200° C. Following the bonding, as shown in FIG. 7, the second handle layer 113 is removed by a wet etch process, such as KOH etching or TMAH etching, and the second buried oxide layer 112 is removed by wet or dry etching such that the lower surface 1112 of the second device layer 111 is exposed and a portion of the second device layer 111, which is now positioned above the cavity 120, is defined as a diaphragm 130.

Figure 8:
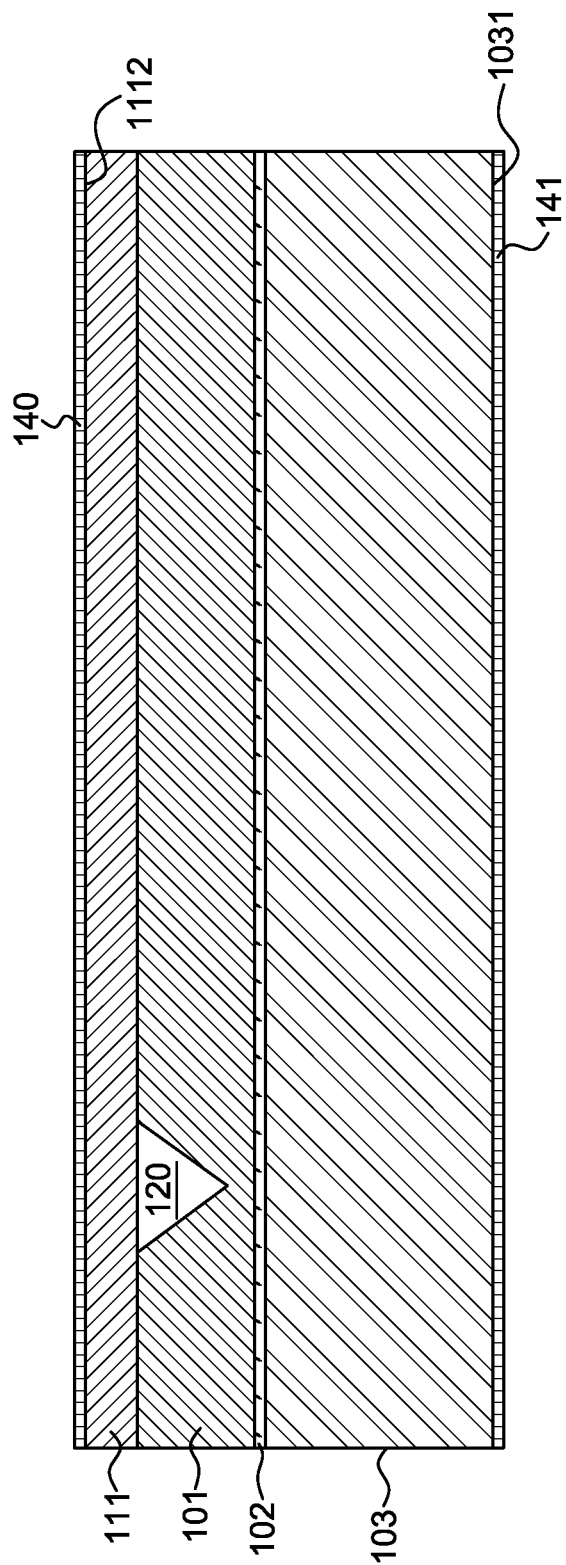
FIG. 8 is a side view of the assembly of FIG. 6 with insulators formed.

With reference to FIG. 8, a first insulator 140 is disposed on the now exposed lower surface 1112 of the second device layer 111 and a second insulator 141 is disposed on a lower surface 1031 of the first handle layer 103. The first insulator 140 and the second insulator 141 may each be provided as a passivation layer, such as, for example, a layer of silicon dioxide or some other electrically non-conductive material. Disposition of the first insulator 140 and the second insulator 141 may be achieved by deposition or growth processes.

Figure 9:
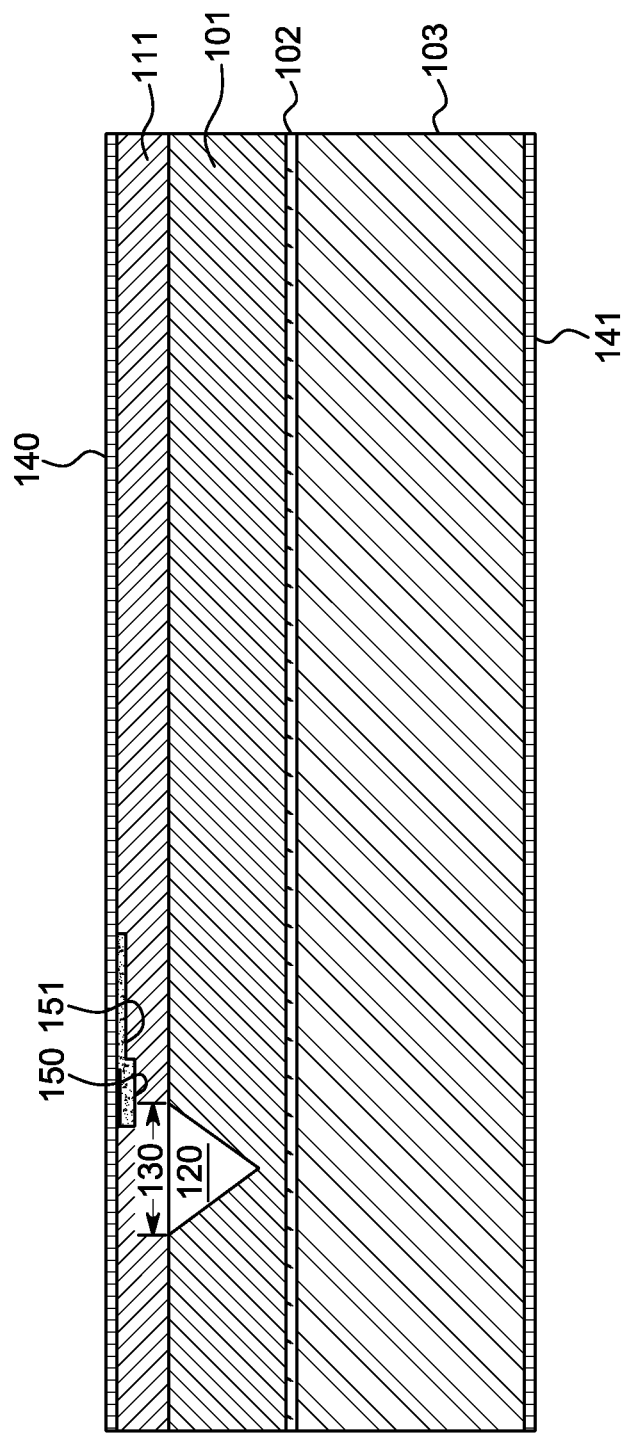
FIG. 9 is a side view of the assembly of FIG. 8 with a piezoresistive pressure sensor and an interconnect portion formed proximate to the cavity.
Figure 10:
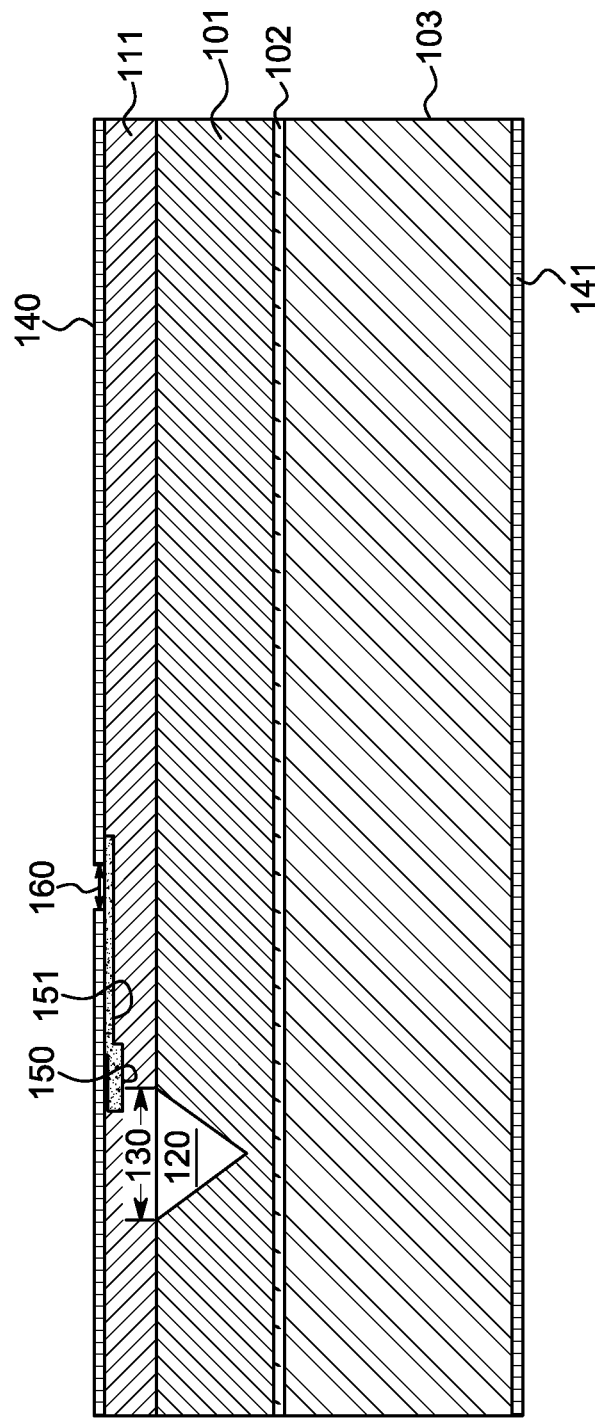
FIG. 10 is a side view of the assembly of FIG. 9 with an opening formed in the insulator to expose a portion of the interconnect portion.

With reference to FIGS. 9 and 10, a piezoresistive pressure sensor 150 and an interconnect portion 151 thereof are then formed in the second device layer 111 such that the piezoresistive pressure sensor 150 is operably disposed proximate to the cavity 120 and the diaphragm 130 (see FIG. 9). Formation of the piezoresistive pressure sensor 150 and the interconnect portion 151 may include at least one or more of p-type dopant diffusion and implantation. At this point, the first insulator 140 insulates the piezoresistive pressure sensor 150 and the interconnect portion 151. Thus, an opening 160 may be defined in the first insulator 140 by at least one or more of wet and dry etching such that at least the interconnect portion 151 of the piezoresistive pressure sensor 150 is exposed through the opening 160 (see FIG. 10).

Figure 11:
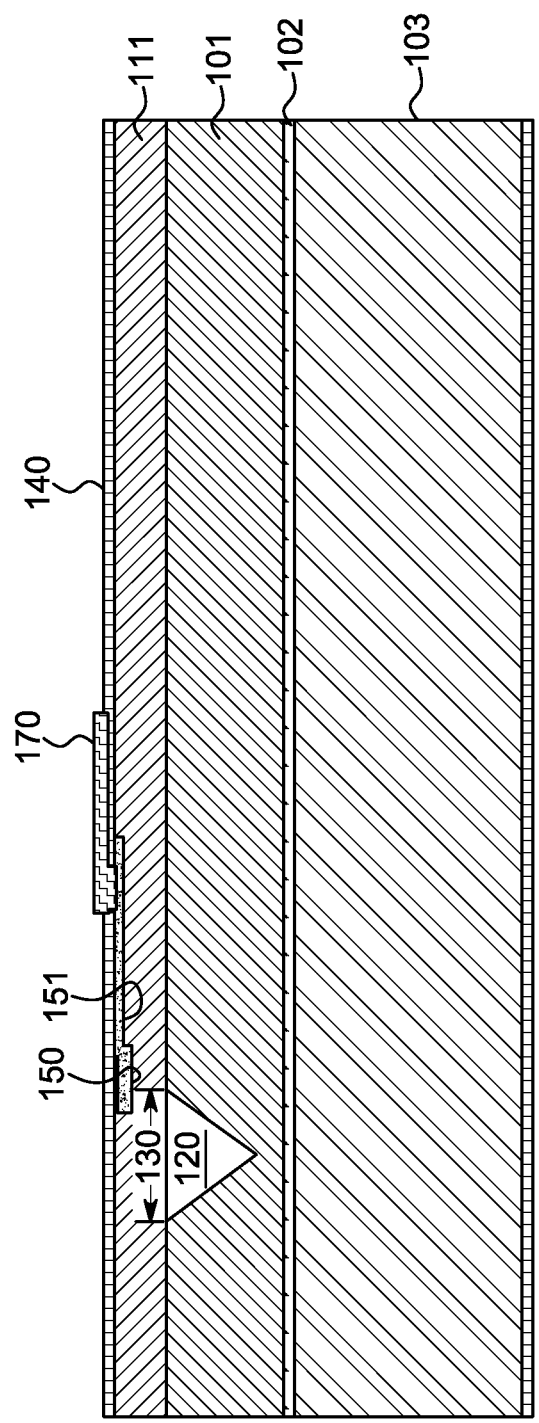
FIG. 11 is a side view of a bond pad electrically coupled to the interconnect portion via the opening.
Figure 12:
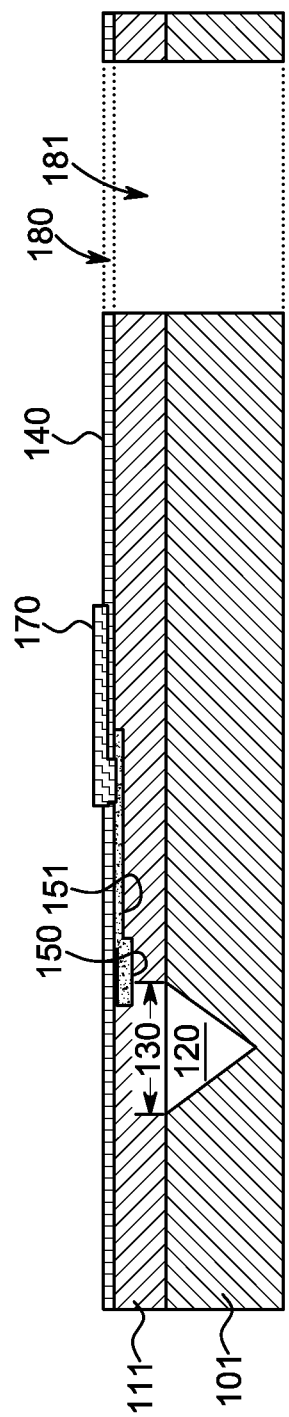
FIG. 12 is a side view of the assembly of FIG. 11 with through-holes formed.

With reference to FIGS. 11 and 12, a first bond pad 170 is electrically coupled to the interconnect portion 151 of the piezoresistive pressure sensor 150 via the opening 160 (see FIG. 11). This operation may be conducted by a metallization process including, for example, deposition processing of a suitable metal or metallic alloy (i.e., aluminum). At this point, as shown in FIG. 12, the first handle layer 103 may be removed by a wet etch process, such as KOH etching or TMAH etching. A first through-hole 180 may then be etched in the first insulator 140, a second through-hole 181 may be etched in the second device layer 111 and the first device layer 101 by wet etching, dry etching or a combination of wet and dry etching and the first buried oxide layer 102 may be removed by wet or dry etching.

Figure 13:
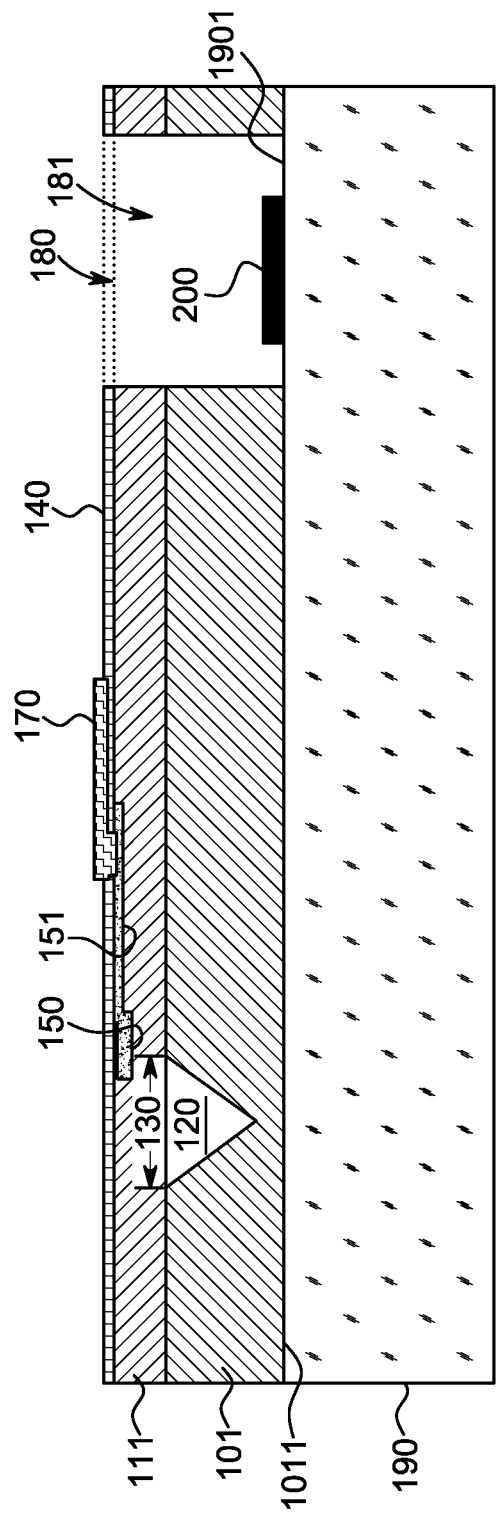
FIG. 13 is a side view of the assembly of FIG. 12 with an insulation layer.
Figure 14:
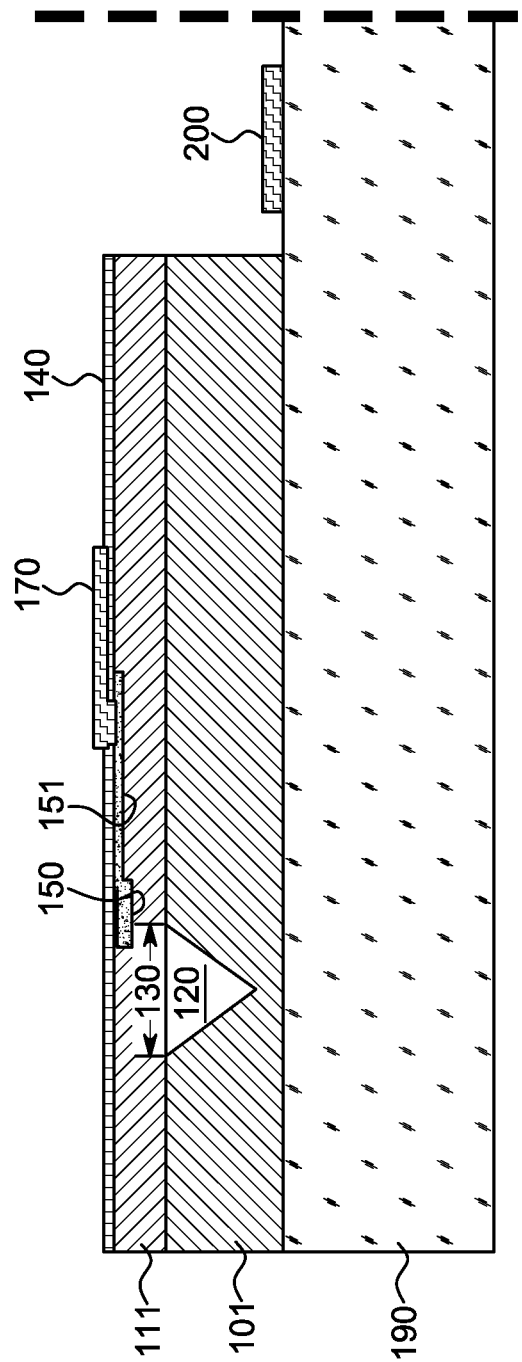
FIG. 14 is a side view of the assembly of FIG. 13 following singulation.

With reference to FIG. 13, an insulation layer 190 is then bonded to the lower surface 1011 of the first device layer 101. The insulation layer 190 may be formed of glass or another suitable electrically non-conductive material and may have a second bond pad 200, which is formed of electrically conductive material, bonded thereto. In accordance with embodiments, the second bond pad 200 may be previously disposed on an upper surface 1901 of the insulation layer 190 such that the second bond pad 200 is exposed through the first through-hole 180 and the second through-hole 181.

Once the insulation layer 190 is bonded to the lower surface 1011 of the first device layer 101, additional processing operations can be undertaken that would otherwise risk damage to the elements described above. These additional processing operations may include, for example, electrically coupling the second bond pad 200 to the first bond pad 170 and, with reference to FIG. 14, singulation processing. During singulation processing, the catheter die 10 is cut out or away from extra material that may be used in the processing of additional catheter dies.

Figure 15:
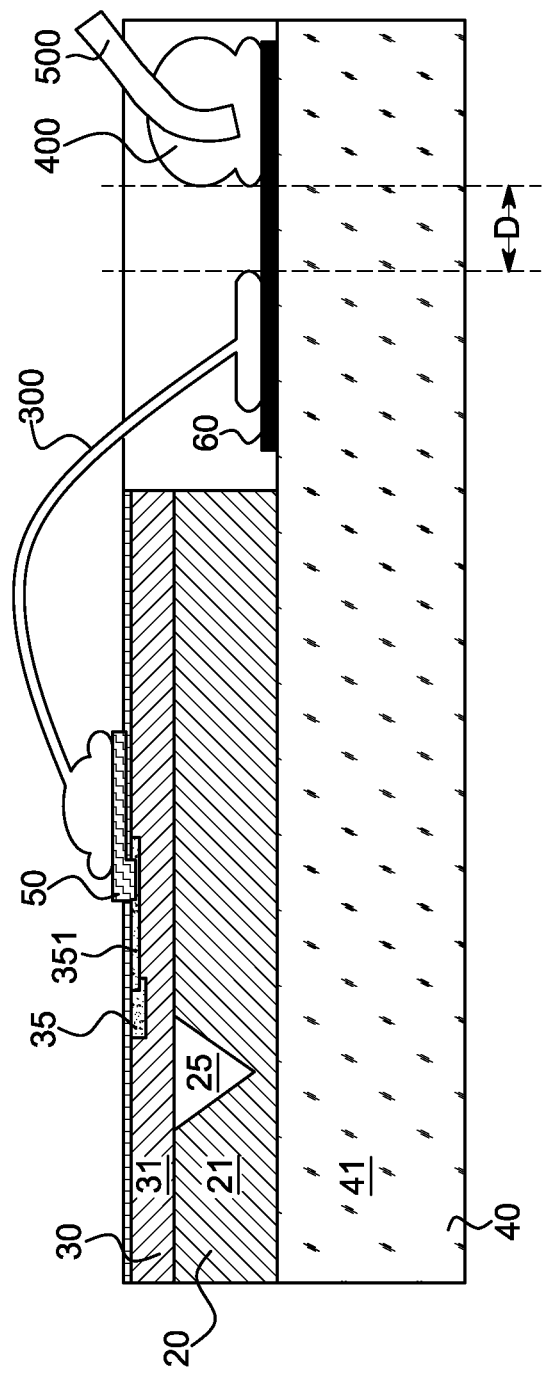
FIG. 15 is a side view of the catheter die of FIG. 1 in accordance with further embodiments of the invention.

In accordance with further aspects of the invention and, with reference to FIGS. 1 and 15, the catheter die 10 of FIG. 1 may be further provided with wiring 300, such as a wire bond, which is configured to electrically couple the first bond pad 50 to a first end of the second bond pad 60. In addition, as shown in FIG. 15, the catheter die 10 may include a solder bond 400 that serves to electrically couple an external connector 500 to a second end of the second bond pad 60. In this case, a distance D between the wiring 300 and the solder bond 400 may be variable and up to 1 mm or more with the insulation layer 40 being substantially longer than the thicknesses of the first device layer 20, the second device layer 30 and the insulation layer 40.

In addition, still referring to FIGS. 1 and 15, it is to be understood that the catheter die 10 may include multiple piezoresistive pressure sensors 35 and a corresponding number of first bond pads 50 and second bond pads 60 as well as a corresponding number of solder bonds 400 and external connectors 500. The multiple first bond pads 50 may be disposed in an axially staggered formation on the insulator 36 thus requiring that the multiple second bond pads 60 also be disposed in a correspondingly staggered formation. In such cases, the multiple solder bonds 400 and the multiple external connectors 500 may also be disposed in a correspondingly staggered formation. Alternatively, if the distance D is sufficiently long (e.g., where the most axially displaced bond pad pair is separated from the corresponding solder bond 400), the multiple solder bonds 400 and the multiple external connectors 500 may be disposed in an aligned formation.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A catheter die, comprising:
   a device layer defining a cavity and including a piezoresistive pressure sensor operably disposed proximate to the cavity and an insulator having an opening and being disposed on an upper surface of the device layer such that a portion of the piezoresistive pressure sensor is exposed through the opening;
   an insulation layer bonded to a lower surface of the device layer;
   first and second bond pads, the first bond pad being electrically coupled to the portion of the piezoresistive pressure sensor via the opening and the second bond pad being disposed on the insulation layer.

2. The catheter die according to claim 1, wherein the insulation layer is formed to define vent channels fluidly communicative with the cavity.

3. The catheter die according to claim 1, wherein a thickness of the device layer is approximately 390 µm or less.

4. The catheter die according to claim 1, wherein a thickness of the insulation layer is approximately 390 µm or less.

5. The catheter die according to claim 1, wherein the device layer comprises silicon and the insulation layer comprises glass.

6. A catheter die, comprising:
   a device layer defining a cavity and including a piezoresistive pressure sensor operably disposed proximate to the cavity and an insulator having an opening and being disposed on an upper surface of the device layer such that a portion of the piezoresistive pressure sensor is exposed through the opening;
   an insulation layer bonded to the lower surface of the device layer;
   a first bond pad electrically coupled to the portion of the piezoresistive pressure sensor via the opening;
   a second bond pad disposed on the insulation layer and electrically coupled to the first bond pad via wiring; and
   an external connector electrically coupled to the second bond pad at a distance from the wiring.

7. The catheter die according to claim 6, wherein the insulation layer is formed to define vent channels fluidly communicative with the cavity.

8. The catheter die according to claim 6, wherein a thickness of the device layer is approximately 390 µm or less.

9. The catheter die according to claim 6, wherein a thickness of the insulation layer is approximately 390 µm or less.

10. The catheter die according to claim 6, wherein the first device layer comprises at least one of an n-type and a p-type semi-conductor, the second device layer comprises an n-type semi-conductor and the insulation layer comprises glass.

11. The catheter die according to claim 6, wherein the distance between the external connector and the wiring is 1 mm or more.

12. A method of fabricating a catheter die, comprising:
   forming, in a device layer having upper and lower surfaces, a cavity recessed from at least the upper surface and a piezoresistive pressure sensor operably disposed proximate to the cavity;

disposing an insulator having an opening on the device layer to expose a portion of the piezoresistive pressure sensor;

bonding an insulation layer to the lower surface of the device layer; and electrically coupling a first bond pad to the portion of the piezoresistive pressure sensor via the opening and disposing a second bond pad on the insulation layer.

13. The method according to claim 12, wherein the forming of the cavity comprises at least one or more of wet and dry etching.

14. The method according to claim 12, wherein the disposing of the insulator comprises at least one or more of depositing and growing a passivation layer.

15. The method according to claim 12, wherein the forming of the piezoresistive pressure sensor comprises at least one or more of dopant diffusion and implantation.

16. The method according to claim 12, further comprising defining the opening by at least one or more of wet and dry etching.

17. The method according to claim 12, wherein the electrical coupling of the first bond pad to the portion of the piezoresistive pressure sensor comprises deposition processing.

18. The method according to claim 12, wherein the disposing of the second bond pad on the insulation layer is conducted prior to the bonding of the insulation layer to the lower surface of the device layer and comprises:

etching a first through-hole in the insulator; and etching a second through-hole in the device layer.

19. The method according to claim 12, further comprising singulation processing.

20. The method according to claim 12, further comprising defining in the insulation layer vent channels fluidly communicative with the cavity.

* * * * *